(12) United States Patent
Mitra et al.

(10) Patent No.: US 6,847,700 B1
(45) Date of Patent: Jan. 25, 2005

(54) METHOD AND APPARATUS FOR DELIVERY OF X-RAY IRRADIATION

(75) Inventors: Kunal Mitra, Melbourne, FL (US); Charles R. Lambert, Indialantic, FL (US)

(73) Assignee: Florida Institute of Technology, Melbourne, FL (US)

(*) Notice: Subject to any disclaimer, the term of this patent is extended or adjusted under 35 U.S.C. 154(b) by 243 days.

(21) Appl. No.: 10/055,068

(22) Filed: Jan. 22, 2002

Related U.S. Application Data
(60) Provisional application No. 60/262,922, filed on Jan. 19, 2001.

(51) Int. Cl.$^7$ ............................................... G21K 1/00
(52) U.S. Cl. ...................................................... 378/145
(58) Field of Search ............................... 378/64, 65, 84, 378/145, 147

(56) References Cited

U.S. PATENT DOCUMENTS

| | | | |
|---|---|---|---|
| 5,001,737 A | * 3/1991 | Lewis et al. | 378/147 |
| 5,101,422 A | * 3/1992 | Thiel et al. | 378/145 |
| 5,327,446 A | 7/1994 | Waynant | |
| 5,370,608 A | 12/1994 | Sahota et al. | |
| 5,707,332 A | 1/1998 | Weinberger | |
| 5,866,914 A | * 2/1999 | Jones | 250/505.1 |
| 5,916,143 A | 6/1999 | Apple et al. | |
| 6,093,141 A | 7/2000 | Mosseri et al. | |
| 6,504,901 B1 | * 1/2003 | Loxley et al. | 378/84 |

OTHER PUBLICATIONS

Bittl, John A. et al., "Clinical Success, Complications and Restenosis Rates with Excimer Laser Coronary Angioplasty," American Journal of Cardiology, 1992, pp. 1533–1539, vol. 70.

Cattaneo, Carlo et al., "A Form of Heat Conduction Equation Which Eliminates the Paradox of Instantaneous Propagation," Comptes Rendus, 1958, pp. 431–433, vol. 247.

Coursey, B.M. et al., "Radionuclide Therapy," Physics Today, Apr. 2000, pp. 25–30.

De Jaegere, P. et al., "Endovascular Stents: Preliminary Clinical Results and Future Developments," Clinical Cardiology, 1993, pp. 369–378, vol. 16.

Ellis, S.G. et al., "Restenosis after Placement of Palmaz–Schatz Stents in Native Coronary Arteries: Initial Results of Multicenter Experience," Circulation, 1992, pp. 1836–1844, vol. 86.

Gannot, Israel et al., "Current Status of Flexible Waveguides for IR Laser Radiation Transmission," IEEE Journal of Selected Topics in Quantum Electronics, 1986, pp. 880–889, vol. 2 No. 4.

(List continued on next page.)

*Primary Examiner*—Harshad Patel
(74) *Attorney, Agent, or Firm*—Saliwanchik, Lloyd & Saliwanchik (57) ABSTRACT

The subject invention pertains to a method and apparatus for generation and/or delivery of x-ray irradiation. The subject invention can be used to deliver x-ray irradiation to an artery in order to prevent restenosis in the artery. For example, a short pulse laser generated ionizing dose of x-ray irradiation can be effectively delivered to the arterial wall using hollow waveguides. The delivery of such a dose can help to prevent restenosis. The use of short pulse x-rays can allow energy to be precisely delivered, and can reduce diffusion of the energy to nearby normal tissue during the exposure. The arterial walls can be irradiated from a cylindrical or conical symmetric mirrored reflective end tip mounted on the end of a hollow waveguide. The subject invention also pertains to a method and apparatus for delivery of x-ray radiation with respect to medical therapies such as tumor necrosis.

37 Claims, 7 Drawing Sheets

OTHER PUBLICATIONS

Ilev, Ilko K. et al., "All–Fiber–Optic Sensor for Liquid Level Measurement," Review of Scientific Instruments, 1999, pp. 2551–2554, vol. 70 No. 5.

Ilev, Ilko K. et al., "Grazing–Incidence–Based Hollow Taper for Infrared Laser–to–Fiber Coupling," Applied Physics Letters, 1999, pp. 2921–2923, vol. 74 No. 20.

Ilev, Ilko K. et al., "Ultraviolet Laser Delivery Using an Uncoated Hollow Taper," IEEE Journal of Quantum Electronics, Aug. 2000, pp. 944–948, vol. 36 No. 8.

Joseph, D.D. et al., "Heat Waves," Reviews of Modern Physics, Jan. 1989, pp. 41–73, vol. 61 No. 1.

Kaminski, W., "Hyperbolic Heat Conduction Equation for Material with a Nonhomogeneous Inner Structure," Journal of Heat Transfer, Aug. 1990, pp. 555–560, vol. 112.

Kim, W.S. et al., "Hyperbolic Heat Conduction Due to Axisymmetric Continuous or Pulse Surface Heat Sources," Journal of Applied Physcis, Dec. 1990, pp. 5478–5485, vol. 68.

Kuczumow, Andrzej et al., "Scheme for X–Ray Tracing in Capillary Optics," Appled Optics, Dec. 1994, pp. 7928–7932, vol. 33 No. 34.

Kumakhov, M.A. et al., "Multiple Reflection From Surface X–Ray Optics," Physics Reports, 1990, pp. 289–350, vol. 191 No. 5, North–Holland.

Kumar, Sunil et al., "Hyperbolic Damped–Wave Models for Transient Light–Pulse Propogation in Scattering Media, " Applied Optics, Jul. 1996, pp. 3372–3378, vol. 35 No. 19.

Kumar, Sunil et al., "Microscale Aspects of Thermal Radiation Transport and Laser Applications," Advances in Heat Transfer, 1999, pp. 187–294, vol. 33, Academic Press, San Diego.

Matsuura, Yuji et al., "Delivery of $F_2$—excimer Laser Light by Aluminum Hollow Fibers," Optics Express, Jun. 2000, vol. 6 No. 13.

Mitra, Kunal et al., Development and Comparison of Models for Light–Pulse Transport through Scattering–Absorbing Media, Jan. 1999, pp. 188–196, vol. 38 No. 1.

Mitra, K. et al., "Experimental Evidence of Hyperbolic Heat Conduction in Processed Meat," Journal of Heat Transfer, 1995, pp. 568–573, vol. 117 No. 3.

Mosher, D. et al., "X radiation from High–Energy–Density Exploded–Wire Discharges," Applied Physics Letter, Oct. 1973, pp. 429–430, vol. 23 No. 8.

Mosher, D. et al., "X–Ray Light Pipes," Applied Physics Letter, Jul. 1976, pp. 105–107, vol. 29 No. 2.

Pepine, Carl J. et al."A Controlled Trial of Corticosteroids to Prevent Restenosis After Coronary Angioplasty," Circulation, Feb. 1990, pp. 1753–1761, vol. 81.

Rindby, A., "Applications of Fiber Technique in the X–Ray Region," Nuclear Instruments and Methods in Physics Research, 1986, pp. 536–540, A249, North–Holland, Amsterdam.

Schatz, Richard A.et al. "Clinical Experience With the Palmaz–Schatz Coronary Stent Initial Results of a Multicenter Study," Circulation, 1991, pp. 148–161, vol. 83.

Serruys, Patrick W. et al. "A Comparison of Balloon–Expandable–Stent Implantation with Balloon Angioplasty in Patients with Coronary Artery Disease," The New England Journal of Medicine, Aug. 1994, pp. 489–495, vol. 331 No. 8.

Teirstein, Paul S. et al., "Two–Year Follow–Up After Catherer–Bases Radiotherapy to Inhibit Coronary Restenosis," Circulation, Jan. 1999, pp. 243–247, vol. 99 No. 2.

Topol, Eric J. et al., "A Comparison of Directional Atherectomy with Coronary Angioplasty in Patients with Coronary Artery Disease," The New England Journal of Medicine, Jul. 1993, pp. 221–227, vol. 329 No. 4.

Vedavarz, Ali et al., "Significance of Non–Fourier Heat Wave in Conduction," ASMW Journal of Heat Transfer, Feb. 1994, pp. 221–224, vol. 116.

Verin, Vitali et al., "Intra–arterial Beta Irradiation Prevents Neointimal Hyperplasia in a Hypercholesterolemic Rabbit Restenosis Model," Ciculation, 1995, pp. 2284–2290, vol. 92 No. 8.

Vernotte, M.P. et al., "Les Paradoxes de la Theorie Coninue de l'Equation de la Chaleur," Comptes Rendus, 1958, pp. 3154–3155, vol. 246.

Waksman, Ron et al., "Endovascular Low–Dose Irradiation Inhibits Neointima Fomation After Coronary Artery Balloon Injury in Swine: A Possible Role for Radiation Therapy in Restenosis Prevention," Circulation, 1995, pp. 1533–1539, vol. 91.

Gannot, I. et al., "Broadband Flexible Waveguides for Free–Electron Laser Radiation," Applied Optics, Sep. 1997, pp. 6289–6293, vol. 36 No. 25.

Weidermann, J.G. et al., "Intracoronary Irradiation Markedly Reduces Neointimal Proliferation After Balloon Angioplasty in Swine: Persistent Benefit at 6–Month Follow–Up," Journal of American College of Cardiology, 1995, pp. 1451–1456, vol. 25.

Whitworth, Hall B. et al., "Effect of Nifedipine on Recurrent Stenosis After Percutaneous Transluminal Coronary Angioplasty," Journal of American College of Cardiology, 1986, pp. 1271–1276, vol. 8 No. 6.

Iler, Ilko K. et al. "Uncoated hollow taper as a simple optical funnel for laser delivery," Review of Scientific Instruments, Oct. 1999, pp. 3840–3843, vol. 70 No. 10.

Spiller, Eberhard et al. "Propagation of x rays in waveguides," Appl. Phys. Lett., Jan. 1974, pp. 60–61, vol. 24 No. 2.

Berg, R. et al. "Time–resolved Transiliumination for Medical Diagnostics" *Time–Resolved Spectroscopy and Imaging of Tissues*, 1991, pp. 110–119, vol. 1431.

Gordon, C.L. et al. "Time–gated Imaging with an Ultrashort––pulse, Laser–product–plasma X–ray Source" *Optics Letters*, 1995, pp. 1056–1058, vol. 20, No. 9.

Milne, P.J. et al. "Development of Sterotactically Guided Laser Interstitial Thermotherapy of Breasr Cancer: In Situ Measurement and Analysis of the Temperature Field in Ex Vivo and In Vivo Adipose Tissue" *Lasers In Surgery and Medicine*, 2000, pp. 67–75, vol. 26.

Rastegar, S. et al. "Hyperbolic Heat Conduction in Pulsed Laser Irradiation of Tissue" *Thermal and Optical Interactions with Biological and Related Composite Materials*, 1989, pp. 114–117, vol. 1064.

Rastegar, S. et al. "An Analysis of Ablation and Thermal Damage in Laser Irradiated Tissue" pp. 119–122.

Sawetprawichkul, A. et al."A Monte carlo Study of the Transient Radiative Transfer within the One–dimensional Multi–layered Slab" *Proceedings of the ASME Heat Transfer Division*, 2000, pp. 145–153, vol. 366–1.

Waynant, R. W. et al. "Transmission Chracteristics of an all–optic–waveguide Biomedical System for X–ray Delivery" *Proceedings of SPIE*, 2002, pp. 121–128, vol. 4615.

Waynant, R. W. et al. "Waveguide Delivery of X–rays for Minimally Invasive Tumor Therapy" *Proceedings of SPIE*, 2001, pp. 492–499, vol. 4244.

* cited by examiner

METHOD AND APPARATUS FOR DELIVERY OF X-RAY IRRADIATION

CROSS-REFERENCE TO A RELATED APPLICATION

This application claims priority from provisional patent application U.S. Ser. No. 60/262,922, filed Jan. 19, 2001.

FIELD OF INVENTION

The subject invention relates to the field of x-ray irradiation, more particularly to the delivery of x-rays to a specific location.

BACKGROUND OF THE INVENTION

Heart and coronary disease is one of the leading causes of mortality in the United States and other parts of the world. When partial or complete closure of a coronary artery occurs a balloon angioplasty is commonly performed to re-open the artery. In this procedure, a catheter is introduced into the coronary artery by access through a small opening in the patient's femoral artery above the thigh. The tip of the catheter has a cylindrical balloon, which is inflated at the site of the blockage and expands the artery, usually compressing the plaque resulting in a substantial increase in blood flow. However, in many cases the plaque quickly accumulates to reclose the artery. This phenomena is called restenosis. It is generally accepted that the most important contributors to restenosis are elastic recoil of the dilated artery, neointimal proliferation, which leads to the thickening of the vessel wall, and unfavorable vascular remodeling, which causes contraction of the artery. Restenosis, after successful coronary angioplasty, is the major limitation to long-term success of the balloon angioplasty.

Despite numerous trials of pharmacological agents, including anticoagulants, corticosteroids, calcium-channels, fish oil, and others, the frequency of restenosis has not diminished (Pepine, C. J., Hirsgfield, J. W., and Macdonald, R. G., "A Controlled Trial of Corticosteroids to Prevent Restenosis after Coronary Angioplasty," Circulation, Vol. 81, pp. 1753–1761 (1990); Whitworth, H. B., Roubin G. S., Hollman, J., Meier, B., Leimgruber, P. P., Douglas, J. S., King, S. B., III, and Gruentzig, A. R., "Effect of Nifedipine on Recurrent Stenosis after Percutaneous Transluminal Coronary Angioplasty," Journal of American College of Cardiology, Vol. 8, pp. 1271–1276 (1986)).

The most common technique currently used for restenosis treatment is placement of stents in arteries after balloon angioplasty. It has been demonstrated that placing stents into arteries after balloon angioplasty successfully addresses remodeling and significantly reduces the restenosis rate (Serruys, P., De Jaegere, P., Kiemeneji, F., Macaya, C., Rutsch, W., Margo, J., Materne, P., Sigwart, U., Colombo, A., Delcan, J., and Morel, M., "A Comparison of Balloon-Expandable-Stent Implantation with Balloon Angioplasty in Patients with Coronary Artery Disease," The New England Journal of Medicine, Vol. 331, no. 8, pp. 489–495 (1994); Ellis, S. G., Savage, M., and Fischman, D., "Restenosis after Placement of Palmaz-Schatz Stents in Native Coronary Arteries: Initial Results of a Multicenter Experience," Circulation, Vol. 86, pp. 1836–1844 (1992)). Though use of stents reduces the restenosis rate, at the same time, stents, as foreign objects in the body, can increase cellular proliferation in surrounding tissue and make the neointimal component of restenosis even worse. Furthermore, the majority of, if not all, stents currently available are metallic and thus thrombogenic. This problem can necessitate anticoagulation therapy (Schatz, R., Baim, D., and Leon, M., "Clinical Experience with the Palmaz-Schatz Coronary Stent," Circulation, Vol. 83, pp. 148–161 (1991)). Anticoagulation therapy can expose the patient to an increases risk of major bleeding and vascular complications (de Jaegere, P., de Feyter, P. J., van der Giessen, W. J., and Serruys, P. W., "Endovascular Stents: Preliminary Clinical Results and Future Developments," Clinical Cardiology, Vol. 16, pp. 369–378 (1993)). Treatment with lasers does not appear to improve the problem of restenosis (Topol, E. J., Leya, F., and Pinkerton, C. A., "A Comparison of Directional Atherectomy with Coronary Angioplasty in Patients with Coronary Artery Disease," The New England Journal of Medicine, Vol. 329, pp. 221–227 (1993); Bittl, J., Sanborn, T., Tcheng J. E., Siegel, R, and Ellis, S. G., "Clinical Success, Complications and Restenosis Rates with Excimer Laser Coronary Angioplasty," American Journal of Cardiology, Vol. 70, pp. 1533–1539 (1992)). It appears that low dose irradiation may inhibit neointimal formation following coronary artery balloon angioplasty. (Waksman, R., Roninson, K. A., Crocker, R., Gravanis, B., Cipolla, G., and King, S., "Endovascular Low Dose radiation Inhibits Neointimal Formation After Coronary Artery Balloon Injury in Swine: A Possible Role for Radiation Therapy in Restenosis Prevention," Circulation, Vol. 91, pp. 1533–1539 (1995); Weidermann, J. G., Marboe, C., Almos, H., Schwartz, A., and Weinberger, J., "Intracoronary Irradiation Markedly Reduces Neointimal Proliferation After Balloon Angioplasty in Swine," Journal of American College of Cardiology, Vol. 25, pp. 1451–1456 (1995); Verin, V., Popovski, Y., Urban, P., Belenger, J., Redard, M., Costa, M., Widmer, M., Rouzaud, M., Nouet, P., Grob, E., Schwager, M., Kurtz, J., and Rutishauser, W., "Intra-arterial Beta Irradiation Prevents Neointimal Hyperplasia in a Hypercholesteroliemic Rabbit: Restenosis Model," Circulation, vol. 92, pp. 2284–2290 (1995); Teirstein, P. S., Massullo, V., Jani, S., Russo, R., Schatz, R., Sirkin, K., Norman, S., and Tripuraneni, P., "Two-Year Follow-Up after Catheter-Based Radiotherapy to Inhibit Coronary Restenosis," Circulation, Vol. 99, no. 2, pp. 243–247 (1999)). Thus, there is a need for a treatment of restenosis which can reduce the drawbacks associated with current treatments.

There is uncertainty as to the healing mechanism of x-ray irradiated injured vessels. Also, it is not clear what long-term side effects of irradiation therapy there may be. It appears that a safe dosage rate is on the order of 8–30 Gy (1 Gy=1 J/kg), while lower radiation doses appear to be unable to significantly inhibit restenosis (Coursey, B. M., and Nath, R., "Radionuclide Therapy," Physics Today, pp. 25–30, April (2000).

SUMMARY OF THE INVENTION

The subject invention pertains to a method and apparatus for generation and/or delivery of x-ray irradiation. The subject method and apparatus provides for the controlled delivery of x-ray radiation to specific parts of a patient's body. The subject invention can be used in the treatment or prevention of restenosis to aid in the prevention of arterial clogging. Additionally, the subject invention is particularly advantageous in situations requiring precise maneuvering due to the lack of radiation generating sources that are introduced into the body as taught by the prior art. Accordingly, there is a need for a method and apparatus for providing a non-invasive procedure which can deliver a highly controlled dose of x-ray radiation to a specific area of the body. In a specific embodiment, the subject invention can be used to deliver x-ray irradiation to an artery in order to prevent restenosis in the artery. For example, a short pulse laser generated ionizing dose of x-ray irradiation can be effectively delivered to the arterial wall using hollow waveguides. The delivery of such a dose can help to prevent restenosis. The accelerating voltage can be adjusted in order to modulate the photon energy, so as to achieve, for example, different depths of penetration. Optimal adjustment of the accelerating voltage can enable maximum effectiveness at minimal dose.

The subject method and apparatus can use hollow waveguides for delivery of short pulse laser generated x-rays through arteries to a target site. The use of short pulse x-rays can allow energy to be precisely delivered, and can reduce diffusion of the energy to nearby normal tissue during the exposure. Compared to radiation in the visible wavelength range, the absorption of radiation in the x-ray region by surrounding tissues can be much lower. For example, the absorption of x-ray radiation can be on the order of 1000 times less. During delivery of x-rays for prevention of restenosis, the lower absorption can allow the x-rays to uniformity penetrate and irradiate the arterial walls.

In a specific embodiment, the arterial walls can be irradiated from a cylindrical or conical symmetric mirrored reflective end tip mounted on the end of a hollow waveguide. The technique can allow the irradiation wavelength to be modulated to achieve a dose which can inhibit plaque growth, instead of limiting the irradiation wavelength based on the maximum voltage the cable can withstand. Utilizing externally laser generated x-rays can avoid the need to insert a miniaturized x-ray tube and high voltage cables inside the arteries. Thus, in addition to patient safety and comfort, the subject invention can enable the entire radiation process to be made safer and simpler for the clinicians who administer it. The subject apparatus and methods can be comparable to systems utilizing conventional optics in both efficiency of delivery and cost. The use of hollow waveguides can produce a homogeneous and high quality smooth Gaussian x-ray beam profile, (Ilev, I. K., and Waynant, R. W., "Grazing-Incidence-Based Hollow Taper for Infrared Laser-to-Fiber Coupling," Applied Physics Letters, Vol. 74, pp. 2921–2923 (1999a); U.S. Pat. No. 5,327,446).

The subject invention also relates to a method for determination of the temperature distribution in an internal tissue, for example, the arterial wall using, for example, a thermographic camera. The data can be validated by, for example, numerical models using a transient radiative transport equation and/or a hyperbolic heat conduction equation.

The subject invention also pertains to a method and apparatus for delivery of x-ray radiation with respect to medical therapies such as tumor necrosis. As compared to utilizing a laser, which is effective for killing tumors near the skin surface, the use of short pulse x-rays can allow irradiation of tumors deeper inside the tissues with minimal harm to normal tissues. The injection of a short pulse x-ray dose via hollow waveguides, such as those found in U.S. Pat. No. 5,327,446 and incorporated herein by reference, allow the delivery of x-rays to a variety of specific locations within the body for a variety of purposes, for example, to enable the treatment of cancer and/or tumors within the body.

In a specific embodiment, the dose from a 3 ns, variable accelerator voltage Fexitron 706, which can produce approximately 50 mrads of x-ray energy, has been concentrated, homogenized, and injected into meter length, sub millimeter hollow waveguides for placement in a simulated tumor in a phantom breast model. Streak and thermal cameras can monitor the energy distribution during the irradiation by observing the distribution of energy as evidenced by fluorescence and by heat. Results from these measurements can be used to optimize the exposure conditions of placement and dose. In order to provide feedback for dosimetry, fiber optics tipped with calibrated scintillators, and strategically located near the tumor, can be used to measure the dose delivered.

DETAILED DESCRIPTION OF THE INVENTION

The subject invention relates to a method and apparatus for the generation and/or delivery of x-rays. In a specific embodiment, the subject invention can utilize hollow waveguides to convey x-ray radiation generated outside of the body into the body to a specific internal surface for a variety of purposes, for example, for medical therapy. For example, the x-ray radiation can be delivered to an arterial wall for the prevention of restenosis following balloon angioplasty. In another embodiment, the x-ray radiation can be delivered into the body to kill tumors with a lesser degree of collateral damage to body tissue than has previously been realized. The x-ray radiation used to treat tumors, for example, can be collected by non-imaging optics and delivered through stereotactically guided needles by hollow waveguides.

X-ray radiation has several applications in the medical field. In addition to imaging, x-rays can be used as a therapy treatment to treat numerous medical conditions. The subject invention can be utilized to control and deliver a precise dose of x-ray radiation to a target location X-ray radiation can be generated for example, by bombarding a metal target with energetic electrons in a vacuum tube. The energy of the x-ray radiation depends on the voltage applied to the vacuum tube. Hollow waveguides have been used for x-ray transmission by D. Mosher, S. J. Stephanakis, I. M. Vitkvovitsky, C. M. Dozier, L. S. Levine and D. J. Nagel, Appl. Phys Lett. 23, pp. 429–431 (1973), D. Mosher and S. J. Stephanakis, "X-ray "light pipes," Appl. Phys. Lett, 29, pp. 105–107 (1976), and M. A. Kumakhov, "Radiation of channeled particles in crystals," Energoatomizdat, Moscow 1986; M. A. Kumakhov, F. F. Komarov, Phys. Rep. 191, p. 289 (1990) and many others. M. A Kuczumow and S. Larsson, "Scheme for x-ray tracing in capillary optics," Appl. Opt. 33, pp.7928–7932, 1994, have also discussed multilayer reflecting surfaces and hollow "capillary optic" waveguides. Short lengths of hollow waveguides can be used to delivery clinically useful doses of radiation to precisely kill tissue with minimal damage to vital tissue nearby.

Figure 1:
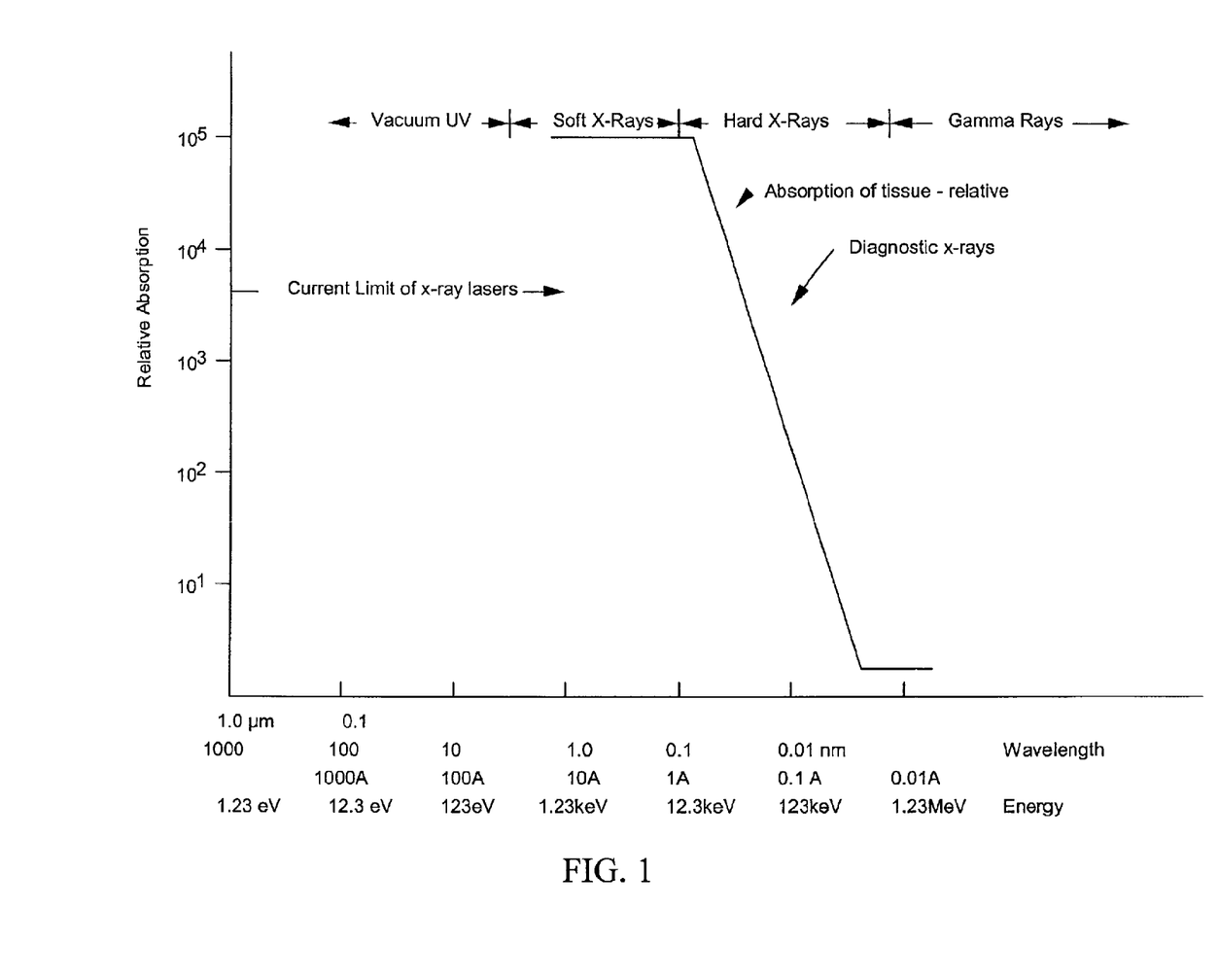
FIG. 1 shows the relationship between x-ray energy and the relative absorption by human tissue.
Figure 6:
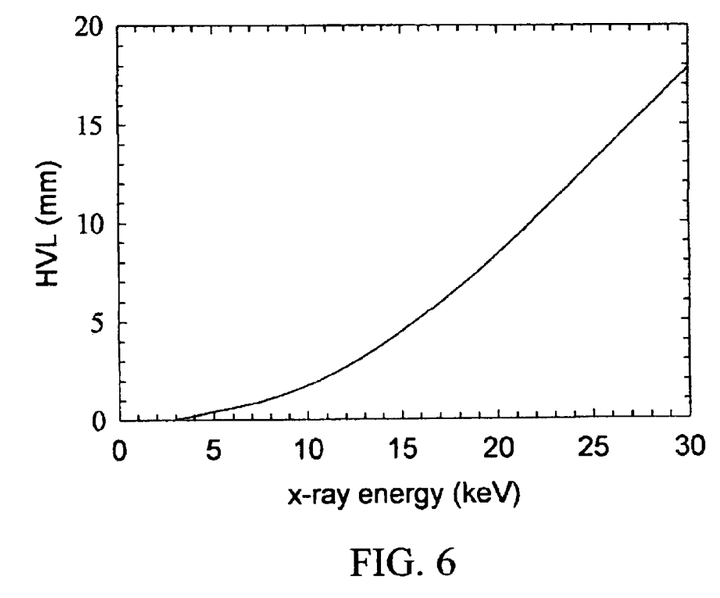
FIG. 6 illustrates the relationship between the x-ray energy and the HVL.

X-ray radiation is absorbed by the body's tissues as the radiation passes through the body. An important parameter is how far the x-ray radiation can propagate in the tissue before it is absorbed. Typically, the intensity of x-ray radiation decreases exponentially as a function of the distance into the tissue that the radiation has passed. Each time the radiation passes through a distance of tissue equal to the half-value layer (HVL), the intensity of the radiation drops by one-half The exact value of the HVL is dependent on the nature of the tissue and the initial intensity of the x-ray radiation. FIG. 6 illustrates the relationship between x-ray energy and the HVL in blood and vascular tissue. As shown, for x-ray radiation on the order of 10 to 20 keV, the HVL ranges from 1.5 to 9 mm. The depth of penetration of x-rays can be controlled by limiting the energy of the x-ray photons as shown in FIG. 1. The control of the energy of x-rays that are transmitted through the waveguides can be enhanced by incorporating Bragg gratings inside the waveguides.

Figure 7:
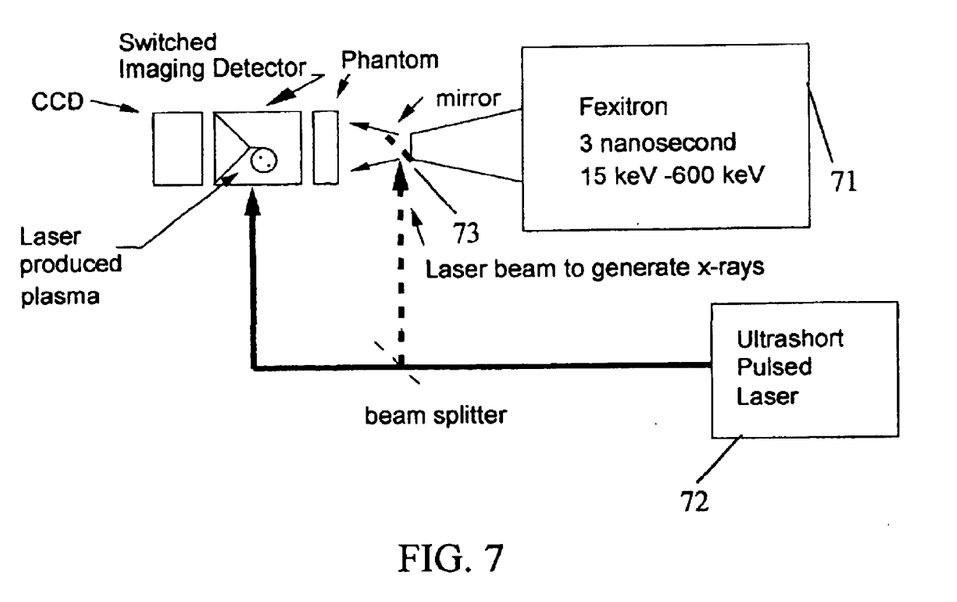
FIG. 7 shows an x-ray generation device in accordance with the subject invention.
Figure 8:
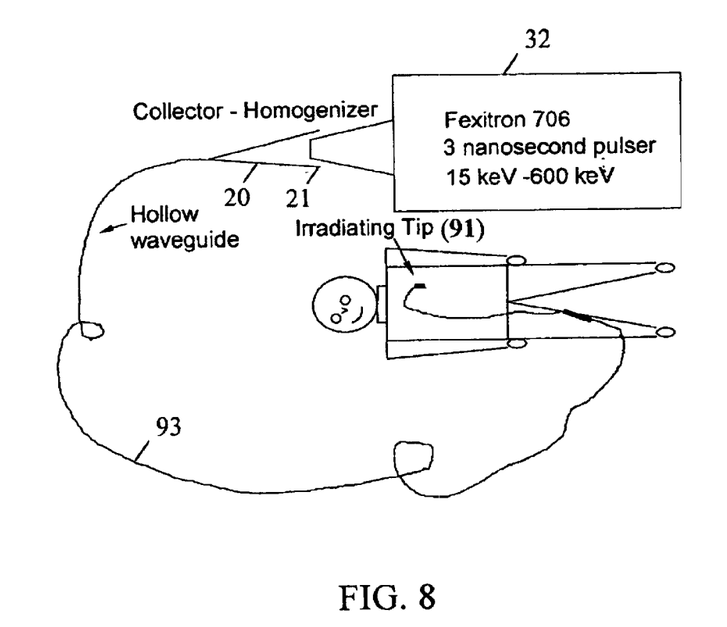
FIG. 8 illustrates an overall view of an arterial treatment in accordance with the subject invention.

FIG. 7 shows a short pulse hard x-ray source and an image switching technique to rapidly form a reflecting electron plasma to gate out the scattered x-rays from the image. Short pulse x-rays can be directly produced by, for example, a Fexitron Marks bank generator 71 or a short pulse laser 72 incident onto a metallic Tantalum target 73 (as shown by dotted lines). Other materials can be used as a target in order to achieve desired x-ray characteristics as a function of wavelength, power, and spatial uniformity. Using these techniques, as well as others known in the art, a wide range of x-ray energies, for example, from 15 to 600 keV, can be produced.

For prevention of restenosis, a radiation dose of about ten to twenty millijoules per gram (equivalent to 10–20 Gray) can be used. Although hollow tapers have been used for coupling laser radiation in the UV, visible, and IR into fibers (Ilev, I. K., and Waynant, R. W., "Grazing-Incidence-Based Hollow Taper for Infrared Laser-to-Fiber Coupling," Applied Physics Letters, Vol. 74, pp. 2921–2923 (1999a); Ilev, I. K., and Waynant, R. W., "Uncoated Hollow Taper as a Simple Optical Funnel for Laser Delivery," Review of Scientific Instrumentation, Vol. 70, pp.3840–3843 (1999b)), hollow tapers have not been demonstrated as practical for coupling x-ray irradiation into fibers. The subject invention uses hollow waveguides and tapered non-imaging elements to deliver x-ray irradiation into a human or animal body to a specific site inside a human or animal body. Depending on the desired use, characteristics of desirable tapers for use with various embodiments of the subject invention can be calculated in accordance with equations set forth in Ilev, I. K., and Waynant, R. W., (1999a) and (1999b), supra. Characteristics of desirable waveguides for use with the subject invention can be designed in accordance with the principles set forth in U.S. Pat. No. 5,327,446 and I. Gannot, R. W. Waynant, A. Inberg, and N. Croitoru "Broadband Flexible waveguides for Free-electron Laser Radiation", Applied Optics, Vol. 36, No. 25, page 6289. A reflective coating can be incorporated on the inner walls of the hollow waveguides and/or tapers in order to enhance their transmission. Uncoated waveguides can be designed to allow grazing incidence of the radiation with respect to the wall of the waveguide. Uncoated tapers can also be designed to allow grazing incidence of the radiation with respect to the wall of the taper. Both coating the inner wall and utilizing grazing incidence can increase reflectance for better hollow waveguide transmission. The subject hollow waveguides can deliver radiation wavelengths from infrared to x-rays. Tapered non-imaging elements can be used to collect the emitted x-ray radiation and reduce the beam spread. The reduced beam can then be inputted into a small hollow waveguide where it can propagate, for example, a few meters. A typical waveguide for this purpose can have a diameter of about 500 $\mu$m. An end reflective device can be used to deliver the x-ray energy in a spatially uniform cylindrical manner.

Figure 3:
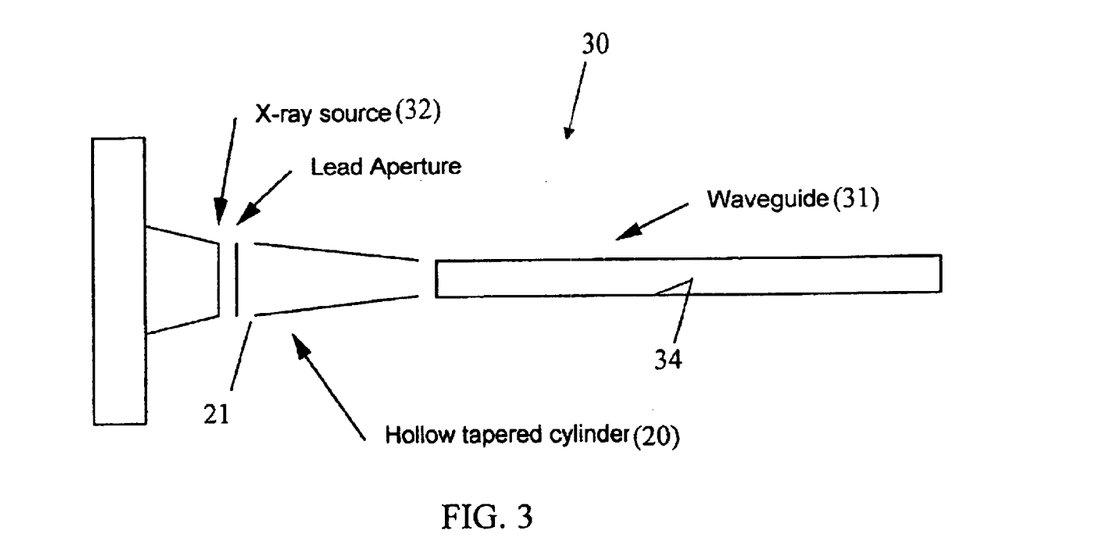
FIG. 3 shows a schematic of an x-ray delivery device in accordance with the subject invention.
Figure 4A:
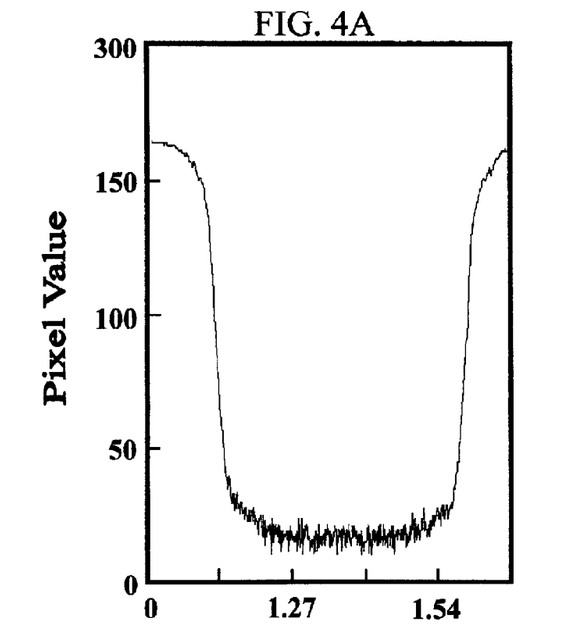
FIGS. 4A–4D show input and output beam profiles with respect to a coupler in accordance with the subject invention.
Figure 4B:
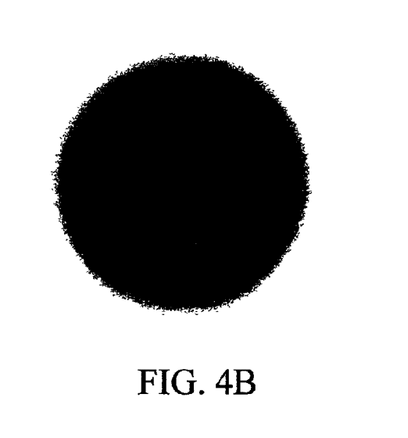
Figure 4C:
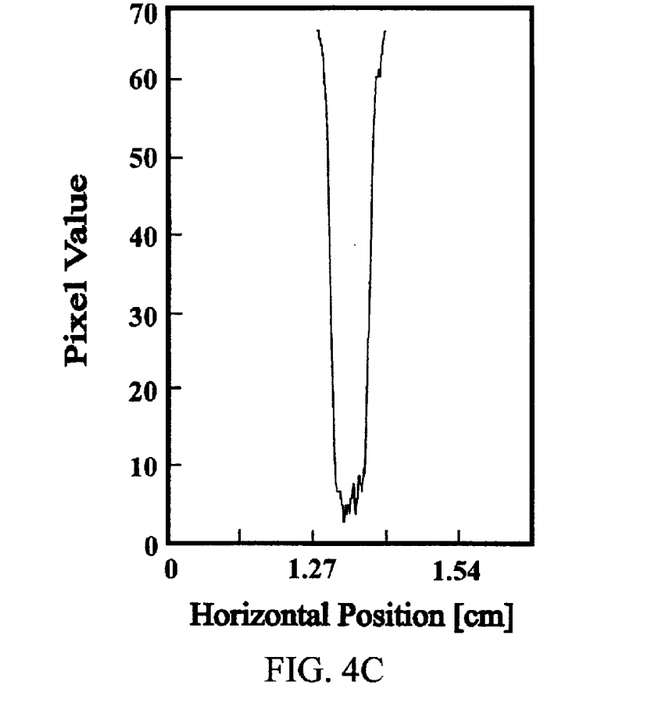
Figure 4D:
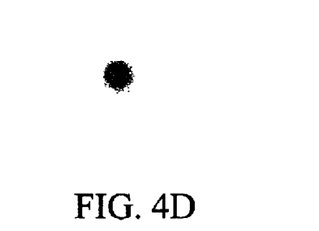

FIG. 3 shows a specific embodiment of a hollow waveguide delivery system 30 for delivery of externally generated short pulse x-rays 32. The subject system offers advantages as compared to research with respect to the use of short pulse x-rays for restenosis treatment currently being undertaken in which an x-ray radiation tube is inserted inside the arteries along with the high voltage cables. In particular, there are advantages to the production of the radiation outside the patient and delivering it through hollow waveguides 31. These systems can rival conventional optics in both efficiency of delivery and in cost. Hollow waveguides can have less attenuation in the x-ray region than at longer wavelengths (the ultraviolet and infrared). The position of the hollow waveguides can be guided with the aid of conventional x-ray to the proper location in the artery, in a manner similar to that used as with balloon angioplasty. The subject method can be accomplished without high voltage cables inserted into a patient and, therefore, can avoid harm to doctors and patients from high voltage. Advantageously, the subject method can provide beam homogeneity, precise aperture of the waveguides allowing precise dose measurements, and minimization of the exposure to normal tissues.

Solid waveguides can also be utilized to transport x-ray irradiation in accordance with the subject invention. Specific embodiments of solid waveguides can incorporate reflective layers in the solid waveguides. With respect to hollow waveguides, reflective coatings can be applied to the inner surface 34 in a variety of methods, as known in the art. In a specific embodiment, the hollow waveguide can be slit open, the reflective coating applied, and the waveguide glued back together. Materials which can be utilized to produce the subject waveguides include, but are not limited to, glass, plastic, and metal.

Figure 9:
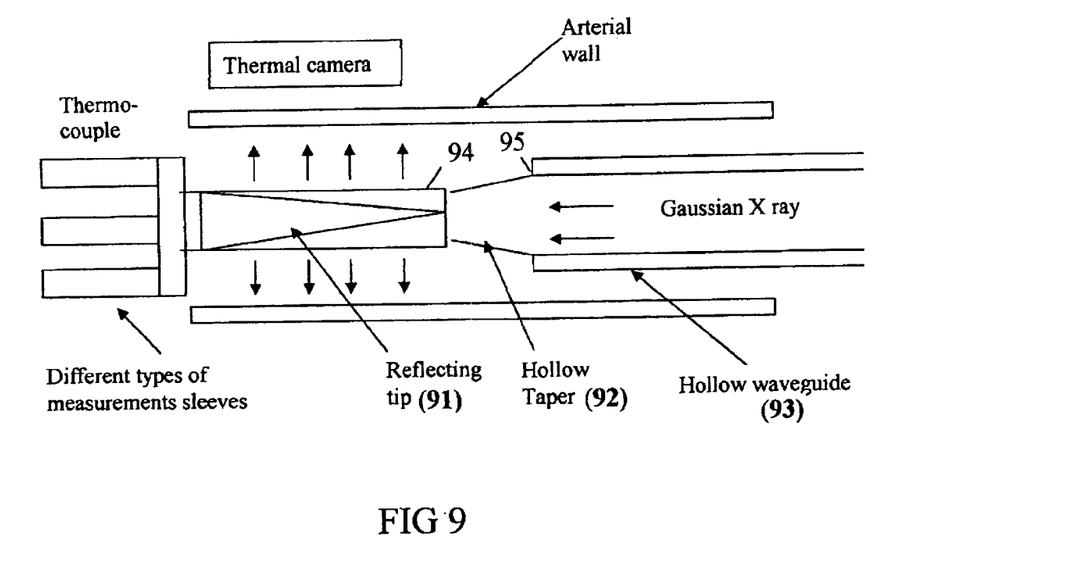
FIG. 9 illustrates a conical reflecting tip in accordance with the subject invention.

In order to produce a uniform, cylindrical pattern of x-ray irradiation pattern on the walls of the artery, a cylindrical or conical reflective tip 91 can be mounted on the end of the hollow taper 92 and waveguide 93 combination as shown in FIG. 9. FIG. 9 shows the hollow taper 92, waveguide 93, and a delivery tip 91. The delivery tip 21 can reflect the radiation uniformly through the clear walls of the glass tube 94 surrounding the tip. As the uniform Gaussian x-ray beam falls over the cylindrical surface of the reflector, the conical tip 91 reflects a uniform irradiation of the walls of the artery. When the x-ray output delivery at the waveguide is multimode, a very small hollow taper 92 at the waveguide output 95 can be used to get smooth Gaussian x-ray beam profile. Reflective tips of various designs can be utilized with the subject invention. For example, the tip can be convex, concave, linear, or any other shape which will produce the desired output pattern of x-ray irradiation toward the target site. In a specific embodiment, the reflecting tip can have a first portion of glass surrounded by a second portion of glass having a different index of refraction than the first portion of glass such that an outer surface of the reflecting tip is cylindrical, such that x-ray irradiation exiting the end of the waveguide and incident on the reflecting tip is reflected at a boundary between the first portion of glass and the second portion of glass.

The subject method can also involve the monitoring of one or more of the following: the source emission, waveguide input and output, and the resulting emission from the final tip. In a specific embodiment, an array of infrared detectors imbedded into the arteries can be used to determine the temporal and spatial pattern of the radiation delivered. Temperature measurements can be performed to help ensure the proper dosage is given. The temperature can be measured by using, for example, a thermographic camera (Bales Scientific) capable of one twentieth of a degree discrimination, and by thermocouples imbedded near the arterial walls. Preferably, the short exposure pulse does not cause temperature migration and the penetration of x-rays uniformly doses the arterial wall. Accordingly, very little normal tissue is exposed. Realistic modeling can be done to determine the proper location of the distal fiber tip once transmission of energy has begun.

Numerical analysis can be performed to optimize the x-ray irradiation as well as thermal response of the tissues. The temperature distribution in any medium absorbing x-rays is primarily dependent on the medium's ability to transmit, absorb, and scatter the incident irradiation and to conduct away the resultant heat. By reliably predicting the resultant temperature fields in arteries and their periphery, the accuracy of the necessary dose for therapeutic outcomes can be improved. In addition to experimental results, the spatial and temporal temperature distribution can be obtained numerically. Such numerical calculations can be used for validation of experimental data Specific numerical calculations can involve solving a couple set of equations—the transient radiative transport equation and the hyperbolic heat conduction equation.

The transient radiative transfer equation for x-ray photon propagation can be written as (Modest, M. F., Radiative Heat Transfer, McGraw Hill (1993); Brewster, M. Q., Thermal Radiative Transfer and Properties, Wiley Interscience (1992); Siegel, R., and Howell, J. R., Thermal Radiation Heat Transfer, 3rd ed., McGraw-Hill, New York (1992)).

$$\frac{1}{c} \frac{\partial I(\vec{r}, \hat{s}, t)}{\partial t} + \hat{s} \cdot \vec{\nabla} I(\vec{r}, \hat{s}, t) = \\ -\sigma_e I(\vec{r}, \hat{s}, t) + \frac{\sigma_s}{4\pi} \int_{4\pi} I(\vec{r}, \hat{s}', t) \Phi(\hat{s}' \to \hat{s}) d\Omega' + S(\vec{r}, \hat{s}, t), \quad (1)$$

where I is the intensity, c is the speed of x-rays (almost same as the speed of light) in the medium, t is the time, σ is the radiative coefficient (subscripts e, s, and a refer to extinction, scattering, absorption, respectively), ŝ is the unit vector in the direction of intensity, Ω' is the solid angle around ŝ', $\vec{r}$ is the spatial location, S is the incident radiation source term, and Φ is the scattering phase function. The above is an integro-differential equation where the partial differentials correspond to hyperbolic differential equations, which yield wave solutions. The equation of transfer is complicated because of the integral on the right side corresponding to the in-scattering gain term.

A variety of techniques have been already studied to solve the above equation for the intensity distribution (Sawetprawichkul, A., Hsu, P., and Mitra, K., "A Monte Carlo Study of the Transient Radiative Transfer within the One-Dimensional Layered Slab," to be presented at International Mechanical Engineering Congress and Exposition, Orlando (Fla.), Nov. 5–10 (2000); Mitra, K., and Kumar, S., "Development and Comparison of Models for Light Pulse Transport Through Scattering Absorbing Media," Applied Optics, Vol. 38, no. 1, pp. 188–196 (1999); Kumar, S., and Mitra, K., "Microscale Aspects of Thermal Radiation Transport and Laser Applications," Advances in Heat Transfer, Vol. 33, pp. 187–294, Academic Press, San Diego (1999); Kumar, S., Mitra, K., and Yamada, Y., "Hyperbolic Damped-Wave Models for Transient Light-Pulse Propagation in Scattering Media," Applied Optics, Vol. 35, no. 19, pp. 3372–3378 (1996)). Different techniques which can be used include discrete ordinates method, Monte Carlo simulation, and spherical harmonics expansion method. Accurate solution of the intensity can yield a more accurate prediction of the temperature distribution.

Once the intensities are obtained, the temperature distribution can be calculated considering the wave model for laser penetration into the tissue and absorption of the intensity within the tissue, which is given by $$-\nabla \cdot \vec{q}(\vec{r}, t) - \omega \rho_b C_b T(\vec{r}, t) + \sigma_a I(\vec{r}, \hat{s}, t) = \rho C \frac{\partial T(\vec{r}, t)}{\partial t}, \quad (2)$$

$$\vec{q}(\vec{r}, t) + \tau \frac{\partial \vec{q}(\vec{r}, t)}{\partial t} = -\kappa \nabla T(\vec{r}, t), \quad (3)$$

where $\vec{q}$ is heat flux, T is the temperature, w is the blood perfusion rate, $r_b$ is the density of blood, $C_b$ is the specific heat of blood, ρ is the density of tissue, C is the specific heat of tissue, κ is the thermal conductivity of tissue, and τ is the thermal relaxation time of tissue. The relaxation time of the tissues can be experimentally obtained (Mitra, K., Kumar, S., Vedavarz, A., and Moallemi, M. K., "Experimental Evidence of Hyperbolic Heat Conduction Waves in Processed Meat," Journal of Heat Transfer, Vol. 117, no. 3, pp. 568–573 (1995)). Equation (3) is the hyperbolic or wave model of heat conduction proposed by Cattaneo, C., "A Form of Heat Conduction Equation Which Eliminates the Paradox of Instantaneous Propagation," Comptes Rendus, Vol. 247, pp. 431–433 (1958) and Vernotte, M. P., "Les Paradoxes de la Theorie Coninue de l'Equation de la Chaleur," Comptes Rendus, Vol. 246, pp. 3154–3155 (1958) and accounts for finite speed of propagation of thermal signals. If the second term on the left hand side of Equation (3) is neglected it becomes the Fourier or parabolic heat conduction model and it implies a physically unrealistic infinite propagation speed of the temperature signal. Equations (2) and (3) can be combined to obtain $$\nabla^2 T = \left( \frac{1}{\alpha} + \frac{\tau \omega \rho_b C_b}{\kappa} \right) \frac{\partial T}{\partial t} + \frac{\tau}{\alpha} \frac{\partial^2 T}{\partial t^2} + \frac{\omega \rho_b C_b}{\kappa} T - \frac{\sigma_a}{\kappa} I - \frac{\sigma_a}{\kappa} \frac{\partial I}{\partial t}, \quad (4)$$

where a is the thermal diffusivity. Equation (4) is a hyperbolic partial-differential equation and yields a finite wave speed ($=\sqrt{\alpha/\tau}$) for the propagation speed of the temperature signals. In the limit t→0, Equation (4) becomes the parabolic or Fourier heat conduction equation.

Figure 10:
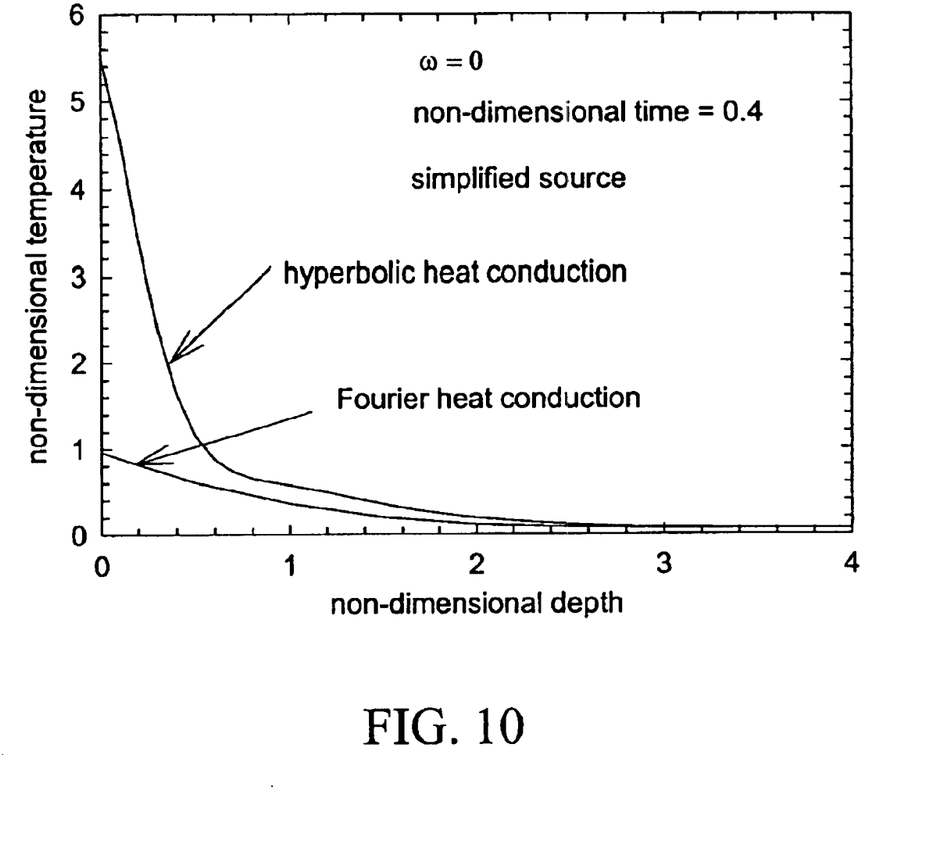
FIG. 10 shows a comparison between hyperbolic and fourier heat conduction equation model.

Most previous work for such analysis have used Fourier heat conduction model. A sample result showing the non-dimensional temperature distribution comparison between hyperbolic and Fourier heat conduction equation is presented in FIG. 10. The case under consideration is a two-dimensional axis-symmetry geometry (r-z coordinate system). It could be seen that there is a significant difference in the temperature profiles between the two cases particularly for regions close to the surface. The use of hyperbolic heat conduction for analyzing short pulse x-ray-tissue interaction characteristics can thus have a tremendous impact on selection of x-ray dosage rates. The same effect is also observed at short time scales and at longer times the temperature profiles match each other (Mitra, K., Kumar, S., Vedavarz, A., and Moallemi, M. K., "Experimental Evidence of Hyperbolic Heat Conduction Waves in Processed Meat," Journal of Heat Transfer, Vol. 117, no. 3, pp. 568–573 (1995)).

The subject invention also involves a delivery apparatus for delivering x-rays to a specific location such as, for example, a tumor inside the body. Such a delivery apparatus can incorporate a coupler to connect the source to a hollow waveguide to transport the x-rays to and into the body. A focusing tip can be positioned on the end of the hollow waveguide to further concentrate the x-rays that traverse the waveguide. Such a focusing tip can be placed in the proper position to irradiate, for example, a tumor. The subject invention can also incorporate means for positioning and guiding the position of the focusing tip. For example, a three-dimensional ultrasound or x-ray information can allow precise stereotactic information on the position of the focusing tip. This information would be useful for any biopsy to determine malignancy and accordingly, could also be used for such a procedure. For example, once a tumor is located, a minimally invasive route could be chosen for insertion of a guidance needle and then a malignancy determination made. If malignant, the guidance needle can be kept in place to guide an eradication waveguide. This can place a premium on rapid analysis of a biopsy. For example, nearly instant "optical biopsies" can be used.

As discussed, the x-ray delivery system can utilize waveguides to guide the radiation into the body. In a specific embodiment, very small hollow glass tubes, for example, with outer diameters less than a millimeter and inner diameters ranging from a few to hundreds of micrometers, can serve as waveguides. In a preferred embodiment, a waveguide having an outer diameter of 770 micrometers and an inner diameter of 550 micrometers can be used. Such a waveguide is small enough to travel through a needle with an inner diameter of less than a millimeter. Preferably, the inner surface of the hollow waveguide is as smooth as possible. Coatings can be placed on the inner wall to optimize the reflection of the walls. Liquid deposition can be used to apply coatings for some materials, and other materials can be applied using vapor deposition. In addition, high reflection coatings known as "super mirrors" can be assembled into small waveguides for guiding hard x-rays. If desired, lead can be applied to the outside of the waveguide to reduce stray radiation.

Figure 2:
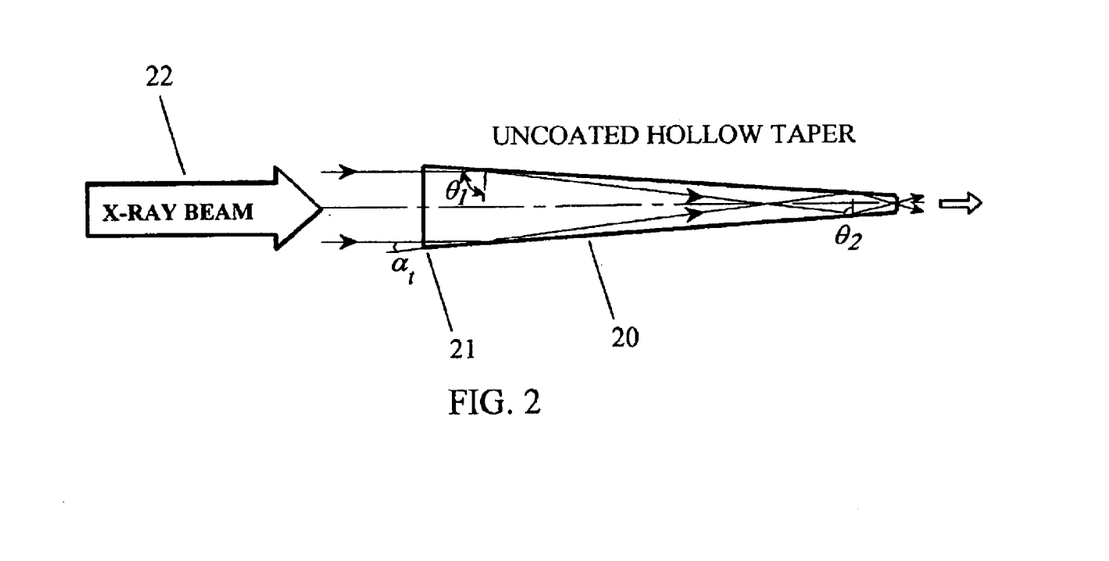
FIG. 2 illustrates a focusing tip in accordance with the subject invention.

With radiation from lasers in the infrared and ultraviolet grazing incidence reflection from cylindrical glass tapers can be used. Theoretical calculations suggest a linear taper is the most efficient taper, and we have been able to produce close approximations to a linear taper in the laboratory. A diagram of a coupling taper 20 is shown in FIG. 2. Preferably, an x-ray source 32 capable of producing a well-columnated beam can deliver an x-ray beam 22 into the wide end 21 of a linear taper in order to couple to the subject waveguide. Other shaped tapers, such as parabolic, can also be utilized with the subject invention.

Further concentration, or expansion, of the x-rays can be done as the beam of radiation leaves the waveguide and irradiates the tumor. In a specific embodiment, focusing or concentration of the beam can be done with another simple linear taper, as used for coupling radiation into the waveguide. This additional linear taper can be smaller in diameter. To cover a large tumor, the subject apparatus can be positioned further away from the tumor so that the natural expansion of the beam can cover the tumor.

An x-ray delivery system in accordance with the subject invention was tested using a pulsed x-ray source (a Fexitron 706 200–600 keV source). This source emitted approximately 50 mrad of x-ray energy. The pulsed radiation was passed through one or more apertures such that the apertured down radiation was collected with a linear tapered coupler and injected into silver coated hollow waveguides. FIGS. 4A–4D show beam profiles at the coupler input and at the coupler output. Energy measured at the waveguide input and output are Iin=1.1 mrads and Iout=0.2 mrads. These measurements of intensity at input and output gives us a transmission of 15–20% for an un-bent waveguide. Measurements of loss as a function of the bending radius can also be taken into consideration.

Dosage amounts for tumor irradiation can be based on the dose needed to accomplish the desired result, taking into account the accepted standards for radiation dose tolerance. Lethal tumor doses typically range from about 20–80 Gy depending on the disease, tumor stage and its location. However, the probability of adverse radiation effects must also be considered, as well as specific patient conditions. Since the subject minimally invasive procedure allows maximum exposure of tumor and minimal irradiation of surrounding normal tissue, it is possible to give sufficient radiation for a high lethality probability and a low probability of adverse results.

To produce a modest dose of about 50 Grays in a tumor two millimeters in diameter, or about 4 mg in weight, about 200 millijoules of absorbed x-ray photons or about $3.12 \times 10^{13}$ photons at 100 keV energy is needed. Assuming delivery of about $10^{11}$ photons per second with a modest x-ray source and fiber delivery, a dose of 50 Grays would require about 5 minutes to administer. This time compares favorably with the time to deliver a thermal dose. In addition, the subject dose is immediately distributed throughout the tumor radiatively, not conductively as with a thermal dose. Such a radiatively distributed dose is a much more controlled dose as compared with a conductively distributed dose.

Figure 5:
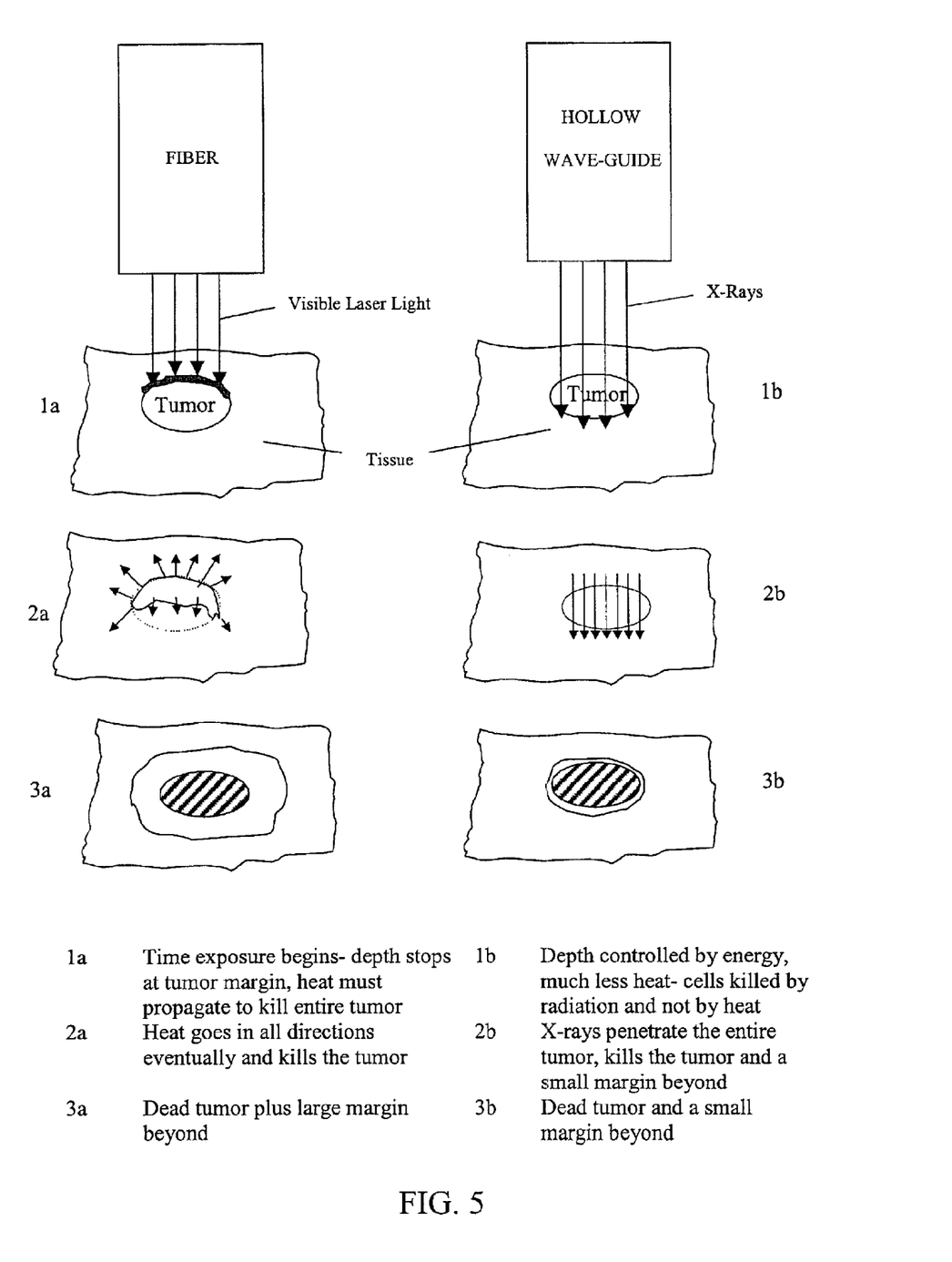
FIG. 5 illustrates a comparison of the mechanism of treating a tumor via thermal treatment and treating a tumor via x-ray irradiation in accordance with the subject invention.

Although the procedure of detecting a tumor and guiding treatment fibers or waveguides to near contact with the tumor is similar for optical and x-ray therapy, there can be significant differences when the radiation is applied. When optical radiation is turned on, nearly all of the radiation is absorbed at the tumor surface. The surface is heated and the heat propagates through the tumor and through the normal tissue as well. Both normal and tumor tissue is killed as the temperature of both increases. While it is permissible and prudent to kill some normal tissue as a precaution or safety margin when there is no vital tissue nearby, when vital tissue is nearby the possibility of thermal damage may be an issue. The risk of such thermal damage may exclude such treatment method as an option. In contrast, when x-ray energy is used, the killing method is different. Tissue is killed by the absorption of a more powerful photon which initiates a chemical interaction that is lethal to the cell that absorbs it. Since a high amount of thermal energy is not required, so there is minimal diffusion of the energy. By delivering a precise beam of x-rays the spread of the killing can be minimized. Vital tissue, if not struck by an x-ray, can continue to function. A schematic comparison of the two techniques is given in FIG. 5.

The conventional methods of generating x-rays can make it difficult to get the x-rays into waveguides. Alternative techniques of x-ray generation, such as first generating very short pulses of optical energy and then using these optical pulses to generate x-rays from plasmas may produce x-rays more easily introduced into waveguides. In addition, short pulses might be less harmful to tissue than longer pulses. Furthermore, short, intense optical pulses can be injected into x-ray emitting structures that can be used to feed waveguides. Although tapers work well with narrow beams, other collecting methods may be preferred for wide beams. For example, Laser generation of x-rays can be done in a manner that takes advantage of light focusing to condense the energy into a narrow beam before generating the x-rays. A parabolic collector may be preferred for wide beams.

All patents, patent applications, provisional applications, and publications referred to or cited herein are incorporated by reference in their entirety to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims.

References

Apple, M., and Apple, M., U.S. Pat. No. 5,916,143, "Brachytherapy Catheter System," Jul. 29 (1999).

Berg, R., Andersson-Engels, S., Jarlman, O., and Svanberg, O., "Time Resolved Transillumination for Medical Diagnostics," SPIE-Time Resolved Spectroscopy and Imaging of Tissue, Vol. 1431, pp. 110–119 (1991).

Bittl, J., Sanborn, T., Tcheng J. E., Siegel, R, and Ellis, S. G., "Clinical Success, Complications and Restenosis Rates with Excimer Laser Coronary Angioplasty," American Journal of Cardiology, Vol. 70, pp. 1533–1539 (1992).

Brewster, M. Q., Thermal Radiative Transfer and Properties, Wiley Interscience (1992).

Cattaneo, C., "A Form of Heat Conduction Equation Which Eliminates the Paradox of Instantaneous Propagation," Comptes Rendus, Vol. 247, pp. 431–433 (1958).

Coursey, B. M., and Nath, R., "Radionuclide Therapy," Physics Today, pp. 25–30, April (2000).

de Jaegere, P., de Feyter, P. J., van der Giessen, W. J., and Serruys, P. W., "Endovascular Stents: Preliminary Clinical Results and Future Developments," Clinical Cardiology, Vol. 16, pp. 369–378 (1993).

Ellis, S. G., Savage, M., and Fischman, D., "Restenosis after Placement of Palmaz-Schatz Stents in Native Coronary Arteries: Initial Results of a Multicenter Experience," Circulation, Vol. 86, pp. 1836–1844 (1992).

Ilev, I. K., and Waynant, R. W., "Grazing-Incidence-Based Hollow Taper for Infrared Laser-to-Fiber Coupling," Applied Physics Letters, Vol. 74, pp. 2921–2923 (1999a).

Ilev, I. K., and Waynant, R. W., "Uncoated Hollow Taper as a Simple Optical Funnel for Laser Delivery," Review of Scientific Instrumentation, Vol. 70, pp. 3840–3843 (1999b).

Joseph, D. D., and Preziosi, L., "Heat Waves," Reviews of Modern Physics," Vol. 61, pp. 41–73 (1989).

Kaminski, W., "Hyperbolic Heat Conduction Equation for Materials with a Nonhomogeneous Inner Structure," Journal of Heat Transfer, Vol. 112, pp. 555–560 (1990).

Kim, W. S., Hector, L. G., and Ozisik, M. N., "Hyperbolic Heat Conduction Due to Axisymmetric Continuous or Pulse Surface Heat Sources," Journal of Applied Physics, Vol. 68, pp. 5478–5485 (1990).

Kumar, S., and Mitra, K., "Microscale Aspects of Thermal Radiation Transport and Laser Applications," Advances in Heat Transfer, Vol. 33, pp. 187–294, Academic Press, San Diego (1999).

Kumar, S., Mitra, K., and Yamada, Y., "Hyperbolic Damped-Wave Models for Transient Light-Pulse Propagation in Scattering Media," Applied Optics, Vol. 35, no. 19, pp. 3372–3378 (1996).

Martin, G. T., and Bowman, H. F., "The Temperature Distribution in Laser Irradiated Tissue with Blood Perfusion," National Heat Transfer Conference, Houston (Tex.), pp. 97–102 (1988).

Milne, P. J., Parel, J-M., Manns, F., Denham, D., Gonzalez-Cirre, X., and Robinson, D., "Development of Stereotactically Guided Laser Interstitial Thermotherapy of Breast Cancer: In Situ Measurement and Analysis of the Temperature Field in Ex Vivo and In Vivo Adipose Tissue," Lasers in Surgery and Medicine, Vol. 26, pp. 67–75 (2000).

Mitra, K., and Kumar, S., "Development and Comparison of Models for Light Pulse Transport Through Scattering Absorbing Media," Applied Optics, Vol. 38, no. 1, pp. 188–196 (1999).

Mitra, K., Kumar, S., Vedavarz, A., and Moallemi, M. K., "Experimental Evidence of Hyperbolic Heat Conduction Waves in Processed Meat," Journal of Heat Transfer, Vol. 117, no. 3, pp. 568–573 (1995).

Modest, M. F., Radiative Heat Transfer, McGraw Hill (1993).

Mosseri, M., and Weshler, Z., U.S. Pat. No. 6,093,141, "Stereotactic Radiotreatment and Prevention," Jul. 25 (2000).

Pepine, C. J., Hirsgfield, J. W., and Macdonald, R. G., "A Controlled Trial of Corticosteroids to Prevent Restenosis after Coronary Angioplasty," Circulation, Vol. 81, pp. 1753–1761 (1990).

Rastegar, S., "Hyperbolic Heat Conduction in Pulsed Laser Irradiation of Tissue," SPIE-Thermal and Optical Interactions with Biological and Related Composite Materials, Vol. 1064, pp. 114–117(1989).

Rastegar, S., Welch, A. J., Hayes, L. J., Pearce, J. A., and Diller, K. R., "An Analysis of Ablation and Thermal Damage in Laser Irradiated Tissue," Advances in Bioengineering, BED-Vol. 8, pp. 119–122 (1988).

Sahota, H., and Kipshidze, N., U.S. Pat. No. 5,370,608, "Apparatus for Minimizing Restenosis," Dec. 6 (1994).

Sawetprawichkul, A., Hsu, P., and Mitra, K., "A Monte Carlo Study of the Transient Radiative Transfer within the One-Dimensional Layered Slab," to be presented at International Mechanical Engineering Congress and Exposition, Orlando (Fla.), Nov. 5–10 (2000).

Schatz, R., Baim, D., and Leon, M., "Clinical Experience with the Palmaz-Schatz Coronary Stent," Circulation, Vol. 83, pp. 148–161 (1991).

Serruys, P., De Jaegere, P., Kiemeneji, F., Macaya, C., Rutsch, W., Margo, J., Materne, P., Sigwart, U., Colombo, A., Delcan, J., and Morel, M., "A Comparison of Balloon-Expandable-Stent Implantation with Balloon Angioplasty in Patients with Coronary Artery Disease," The New England Journal of Medicine, Vol. 331, no. 8, pp. 489–495 (1994).

Siegel, R, and Howell, J. R., Thermal Radiation Heat Transfer, 3rd ed., McGraw-Hill, New York (1992).

Teirstein, P. S., Massullo, V., Jani, S., Russo, R., Schatz, R., Sirkin, K., Norman, S., and Tripuraneni, P., "Two-Year Follow-Up after Catheter-Based Radiotherapy to Inhibit Coronary Restenosis," Circulation, Vol. 99, no. 2, pp. 243–247 (1999).

Topol, E. J., Leya, F., and Pinkerton, C. A., "A Comparison of Directional Atherectomy with Coronary Angioplasty in Patients with Coronary Artery Disease," The New England Journal of Medicine, Vol. 329, pp. 221–227 (1993).

Vedavarz, A., Kumar, S., and Moallemi, M. K., "Significance of Non-Fourier Heat Wave in Conduction," ASME Journal of Heat Transfer, Vol. 116, pp. 221–224 (1994).

Verin, V., Popovski, Y., Urban, P., Belenger, I., Redard, M., Costa, M., Widmer, M., Rouzaud, M., Nouet, P., Grob, E., Schwager, M., Kurtz, J., and Rutishauser, W., "Intra-arterial Beta Irradiation Prevents Neointimal Hyperplasia in a Hypercholesteroliemic Rabbit: Restenosis Model," Circulation, vol. 92, pp. 2284–2290 (1995).

Vernotte, M. P., "Les Paradoxes de la Theorie Coninue de l'Equation de la Chaleur," Comptes Rendus, Vol. 246, pp. 3154–3155 (1958).

Waksman, R., Roninson, K. A., Crocker, R., Gravanis, B., Cipolla, G., and King, S., "Endovascular Low Dose Irradiation Inhibits Neointimal Formation After Coronary Artery Balloon Injury in Swine: A Possible Role for Radiation Therapy in Restenosis Prevention," Circulation, Vol. 91, pp. 1533–1539 (1995).

Waynant, R., U.S. Pat. No. 5,327,446, "Method of Exciting Laser Action and Delivering Laser Energy For Medical and Scientific Applications," Jul. 5 (1994).

Weinberger, J., U.S. Pat. No. 5,707,332, "Apparatus and Method to Reduce Restenosis After Arterial Intervention," Jan. 13 (1998).

Weidermann, J. G., Marboe, C., Almos, H., Schwartz, A., and Weinberger, J., "Intracoronary Irradiation Markedly Reduces Neointimal Proliferation After Balloon Angioplasty in Swine," Journal of American College of Cardiology, Vol. 25, pp. 1451–1456 (1995).

Whitworth, H. B., Roubin G. S., Hollman, J., Meier, B., Leimgruber, P. P., Douglas, J. S., King, S. B., III, and Gruentzig, A. R., "Effect of Nifedipine on Recurrent Stenosis after Percutaneous Transluminal Coronary Angioplasty," Journal of American College of Cardiology, Vol. 8, pp. 1271–1276 (1986).

I. Gannot, A. Inberg, N. Croitoru and R. Waynant, "Flexible Waveguides for Free Electron Laser Radiation Transmission," Appl. Opt. 36, pp. 6289–6293, 1996.

I. Gannot, A. Inberg, M. Oksman, R Waynant and N. Croitoru, "Flexible Waveguides for Infrared Laser Radiation," IEEE JSTQE 2, pp. 880–889, 1996.

I. K. Ilev and R. W. Waynant, "Grazing-Incidence-Based Hollow Taper for Infrared Laser-to-Fiber Coupling," Appl. Phys. Lett 74, pp. 2921–2923, 1999.

I. K. Ilev and R. W. Waynant, "All-Fiber-Optic Sensor for Liquid Level Measurement," Rev. Sci. Instrum. 70, pp. 2551–2554, 1999.

I. K. Ilev, R. W. Waynant, M. N. Ediger and M. A. Bonaguidi, "Ultraviolet laser delivery using an uncoated hollow taper," IEEE J. Quantum Electron. 36, pp. 944–948, 2000.

Yuji Matsuura, Takashi Yamamoto and Mitsunobu Miyagi, "Delivery of F2-excimer laser light by aluminum hollow fibers," Optics Express 6, pp. 257–261, 2000.

D. Mosher, S. J. Stephanakis, I. M. Vitkvovitsky, C. M. Dozier, L. S. Levine and D. J. Nagel, Appl. Phys Lett. 23, pp. 429–431, 1973.

D. Mosher and S. J. Stephanakis, "X-ray "light pipes," Appl. Phys. Lett, 29, pp. 105–107, 1976.

M. A. Kumakhov, "Radiation of channeled particles in crystals," Energoatomizdat, Moscow 1986; M. A. Kumakhov, F. F. Komarov, Phys. Rep. 191, p. 289 1990.

A. Rindby, "Applications of Fiber Technique in the x-ray region," Nucl. Instr. And Meth in Phys. Res. A249, pp. 536–540, 1986.

E. Spiller and A. Segmuller, "Propagation of x-rays in waveguides," Appl. Phys. Lett. 24, pp. 60–61, 1973.

A. Kuczumow and S. Larsson, "Scheme for x-ray tracing in capillary optics," Appl. Opt. 33, pp.7928–7932, 1994.

What is claimed is:

1. An apparatus for delivery of x-ray irradiation to a target, comprising:
   a waveguide for transporting x-ray irradiation, the waveguide comprising a first end and second end;
   a means for coupling x-ray irradiation into the first end of the waveguide, wherein the means for coupling x-ray irradiation into the first end of the waveguide comprises a first tapered cylinder; and
   a means for directing the x-ray irradiation exiting the second end of the waveguide to a target.

2. The apparatus according to claim 1, wherein the waveguide is a hollow waveguide.

3. The apparatus according to claim 2, wherein the hollow waveguide comprises a reflective layer on an inner surface of the hollow waveguide.

4. The apparatus according to claim 3, wherein the reflective layer is a super mirror.

5. The apparatus according to claim 3, wherein the hollow waveguide propagates an approximately homogenous approximately Gaussian x-ray beam.

6. The apparatus according to claim 1, wherein the first tapered cylinder is a hollow tapered cylinder.

7. The apparatus according to claim 6, wherein the first tapered cylinder reduces the cross-sectional area of the x-ray irradiation entering the first tapered cylinder as the x-ray irradiation traverses the first tapered cylinder and is coupled into the first end of the waveguide.

8. The apparatus according to claim 6, wherein the means for directing the x-ray irradiation exiting the second end of the waveguide to a target comprises a reflecting tip such that the x-ray irradiation exiting the second end of the waveguide is incident on the reflecting tip and is reflected by the reflecting tip to the target.

9. The apparatus according to claim 8, wherein the reflecting tip comprises a first portion of glass surrounded by a second portion of glass having a different index of refraction than the first portion of glass such that an outer surface of the reflecting tip is cylindrical, wherein x-ray irradiation exiting the second end of the waveguide and incident on the reflecting tip is reflected at a boundary between the first portion of glass and the second portion of glass.

10. The apparatus according to claim 9, wherein the target has a generally cylindrical shape and is generally concentric with the outer surface of the reflecting tip, wherein the reflecting tip reflects the x-ray irradiation in an approximately cylindrical pattern.

11. The apparatus according to claim 10, wherein the reflecting tip comprises a glass outer wall through which the x-ray irradiation passes after being reflected by the reflecting tip.

12. The apparatus according to claim 10, wherein the boundary between the first portion of glass the second portion of glass is conically symmetric about a central axis of the waveguide.

13. The apparatus according to claim 8, further comprising:
   a means for receiving x-ray irradiation exiting the second end of the waveguide and outputting the x-ray irradiation such that the outputted x-ray irradiation is incident on the reflecting tip.

14. The apparatus according to claim 13, wherein the means for receiving x-ray irradiation exiting the second end of the waveguide and outputting the x-ray irradiation such that the outputted x-ray irradiation is incident on the reflecting tip is a second tapered cylinder.

15. The apparatus according to claim 14, wherein the second tapered cylinder is a hollow tapered cylinder.

16. The apparatus according to claim 15, wherein the cross-sectional area of the x-ray irradiation beam outputted from the second hollow tapered cylinder is smaller than the x-ray irradiation beam received by the second hollow tapered cylinder.

17. The apparatus according to claim 15, wherein the x-ray irradiation beam exiting the second hollow tapered cylinder is an approximately homogeneous approximately Gaussian x-ray irradiation beam.

18. The apparatus according to claim 6, wherein the hollow tapered cylinder is a hollow linear tapered cylinder.

19. The apparatus according to claim 1, further comprising:
   a means for generating x-ray irradiation.

20. The apparatus according to claim 19, wherein the means for generating x-ray irradiation comprises a means for generating short pulses of optical energy and a means for using the short pulses of optical energy to generate x-rays from a plasma.

21. A method of selectively delivering x-ray irradiation to a specific location on an internal surface of a human or animal body, comprising:
   selecting a specific location on an internal surface of a human or animal body to which delivery of x-ray irradiation is desired;
   generating x-ray irradiation external to the human or animal body;
   transporting via a waveguide the x-ray irradiation inside the human or animal body; and
   delivering the x-ray irradiation to the specific location.

22. The method according to claim 21, wherein the specific location is a portion of an inner arterial wall of an artery.

23. The method according to claim 22, wherein the inner arterial wall of the artery is irradiated after balloon angioplasty is performed on the artery.

24. The method according to claim 22, wherein a distal end of the waveguide is inserted into the artery to be irradiated and guided within the artery until the distal end reaches the specific location.

25. The method according to claim 24, wherein the waveguide propagates an approximately homogeneous approximately Gaussian x-ray beam.

26. The method according to claim 24, wherein delivering the x-ray irradiation to the specific location comprises reflecting the x-ray irradiation exiting the distal end of the waveguide toward the specific location via a reflective tip.

27. The method according to claim 26, wherein the reflective tip comprises a glass outer wall through which the x-ray irradiation passes after being reflected by a reflective portion of the reflective tip.

28. The method according to claim 26, wherein the reflective tip is conically symmetric about a central axis of the waveguide.

29. The method according to claim 28, wherein an approximately cylindrical pattern of x-ray irradiation on the inner arterial wall is produced.

30. The method according to claim 24, wherein an x-ray irradiation beam exiting the distal end of the waveguide is coupled into a second tapered cylinder, wherein the x-ray irradiation beam exiting the second tapered cylinder has a smaller cross-sectional area than the x-ray irradiation coupled into the second tapered cylinder.

31. The method according to claim 21, wherein the specific location is a tumor, and wherein sufficient x-ray irradiation is delivered to the tumor such that at least a portion of the tumor is necrotized.

32. The method according to claim 21, wherein generating x-ray irradiation comprises generating short pulses of optical energy and using the short pulses of optical energy to generate x-rays from a plasma.

33. The method according to claim 21, wherein transporting via a waveguide the x-ray irradiation inside the human or animal body comprises transporting via a hollow waveguide the x-ray irradiation inside the human or animal body.

34. The method according to claim 33, wherein the hollow waveguide has a reflective coating on an inner surface of the hollow waveguide.

35. The method according to claim 34, wherein the reflective coating on the inner surface of the hollow waveguide is a super mirror.

36. The method according to claim 33, wherein the x-ray irradiation generated external to the body is coupled into the waveguide via a tapered cylinder.

37. The method according to claim 36, wherein the tapered cylinder is a hollow tapered cylinder.

* * * * *

UNITED STATES PATENT AND TRADEMARK OFFICE
CERTIFICATE OF CORRECTION

PATENT NO. : 6,847,700 B1
DATED : January 25, 2005
INVENTOR(S) : Mitra et al.

It is certified that error appears in the above-identified patent and that said Letters Patent is hereby corrected as shown below:

Column 2,
Line 23, "radiation" should read -- Irradiation --.

Column 4,
Line 59, "location X-ray" should read -- location. X-ray --.

Column 8,
Line 59, "parabolic beat" should read -- parabolic heat --.

Column 13,
Line 14, "Belenger, I.," should read -- Belenger, J., --.

Signed and Sealed this

Seventh Day of June, 2005

JON W. DUDAS
*Director of the United States Patent and Trademark Office*